(12) United States Patent
Viellerobe et al.

(10) Patent No.: US 8,237,131 B2
(45) Date of Patent: Aug. 7, 2012

(54) SYSTEM AND METHOD FOR CARRYING OUT FIBRE-TYPE MULTIPHOTON MICROSCOPIC IMAGING OF A SAMPLE

(75) Inventors: Bertrand Viellerobe, Nogent sur Marne (FR); Francois Lacombe, Chaville (FR); Alexandre Loiseau, Paris (FR); Frederic Louradour, Eymoutiers (FR); Mickael Lelek, Brive la Gaillarde (FR); Alain Barthelemy, Limoges (FR); Dominique Pagnoux, Limoges (FR)

(73) Assignees: Mauna Kea Technologies, Paris (FR); Centre National de la Recherche Scientifique, Paris (FR); Universite de Limoges, Limoges (FR)

( * ) Notice: Subject to any disclaimer, the term of this patent is extended or adjusted under 35 U.S.C. 154(b) by 126 days.

(21) Appl. No.: 11/665,768

(22) PCT Filed: Oct. 21, 2005

(86) PCT No.: PCT/FR2005/002630
§ 371 (c)(1),
(2), (4) Date: Apr. 19, 2007

(87) PCT Pub. No.: WO2006/045936
PCT Pub. Date: May 4, 2006

(65) Prior Publication Data
US 2007/0290145 A1    Dec. 20, 2007

(30) Foreign Application Priority Data
Oct. 22, 2004   (FR) ...................................... 04 11313

(51) Int. Cl.
G21K 5/04           (2006.01)

(52) U.S. Cl. .................................................... 250/458.1
(58) Field of Classification Search ................ 250/458.1
See application file for complete search history.

(56) References Cited

U.S. PATENT DOCUMENTS 4,655,547 A * 4/1987 Heritage et al. .............. 359/563
(Continued)

FOREIGN PATENT DOCUMENTS

GB          2 338 568         12/1999
(Continued)

OTHER PUBLICATIONS

Helmchen Miniaturization of fluorescence microscopes using fibre optics, Experimental Physiology, vol. 87, No. 6 (Nov. 1, 2002), pp. 737-745.*

(Continued)

*Primary Examiner* — David Porta
*Assistant Examiner* — Shun Lee
(74) *Attorney, Agent, or Firm* — Osha • Liang LLP

(57) ABSTRACT

A system for carrying out fibered multiphoton microscopic imagery of a sample (10) for use in endoscopy or fluorescence microscopy includes: a femtosecond pulsed laser (1, 2) for generating a multiphoton excitation laser radiation; an image guide (8) having a number of optical fibers and permitting the sample to be illuminated by a point-by-point scanning in a subsurface plane; pre-compensating elements (4) for pre-compensating for dispersion effects of the excitation pulses in the image guide (8), these elements being situated between the pulsed laser and the image guide (8); scanning elements for directing, in succession, the excitation laser beam in a fiber of the image guide, and; in particular, an optical head (9) for focussing the excitation laser beam exiting the image guide in the sample (10).

24 Claims, 8 Drawing Sheets

U.S. PATENT DOCUMENTS

| | | | |
|---|---|---|---|
| 5,606,445 A * | 2/1997 | Kikuchi et al. | 398/147 |
| 5,995,281 A | 11/1999 | Simon et al. | |
| 6,249,630 B1 | 6/2001 | Stock et al. | |
| 6,369,928 B1 | 4/2002 | Mandella et al. | |
| 6,449,039 B1 * | 9/2002 | Bouzid | 356/318 |
| 2005/0242298 A1 | 11/2005 | Genet et al. | |

FOREIGN PATENT DOCUMENTS

| | | |
|---|---|---|
| JP | 10068889 A | 3/1998 |
| JP | 10186424 A | 7/1998 |
| JP | 2003-344777 | 12/2003 |
| WO | 2004/010377 A1 | 1/2004 |
| WO | WO 2004008952 A1 * | 1/2004 |

OTHER PUBLICATIONS

Pogue et al. Fiber-optic bundle design for quantitative fluorescence measurement from tissue, Applied Optics vol. 37, No. 31 (Nov. 1998), pp. 7429-7436.*

CeramOptec Industries, Inc. Data Sheet for Fiber Optic Bundles (May 2003), 2 pages.*

CeramOptec Industries, Inc. Data Sheet for OPTRAN UV, OPTRAN WF (May 2003), 4 pages.*

Helmchen et al. A miniature head-mounted two-photon microscope: high-resolution brain imaging in freely moving animals, Neuron vol. 31 (Sep. 2001), pp. 903-912.*

Helmchen et al. Enhanced two-photon excitation through optical fiber by single-mode propagation in a large core. Applied Optics vol. 41, No. 15 (May 2002), pp. 2930-2934.*

Clark S.W. et al. "Fiber delivery of femtosecond pulses from a Ti:sapphire laser" Optics Letters vol. 26, No. 17 Sep. 1, 2001 pp. 1320-1322.

Göel W. et al. "Distortion-free delivery of nanojoule femtosecond pulses from a Ti:sapphire laser through a hollow-core photonic crystal fiber" Optics Letters vol. 29, No. 11 Jun. 1, 2004 pp. 1285-1287.

Australian Office Action for Application No. 2005298494, mailed on Jul. 19, 2010 (4 pages).

Japanese Office Action for Application No. 2007-537342, mailed on Apr. 26, 2011, and English translation thereof (6 pages).

* cited by examiner

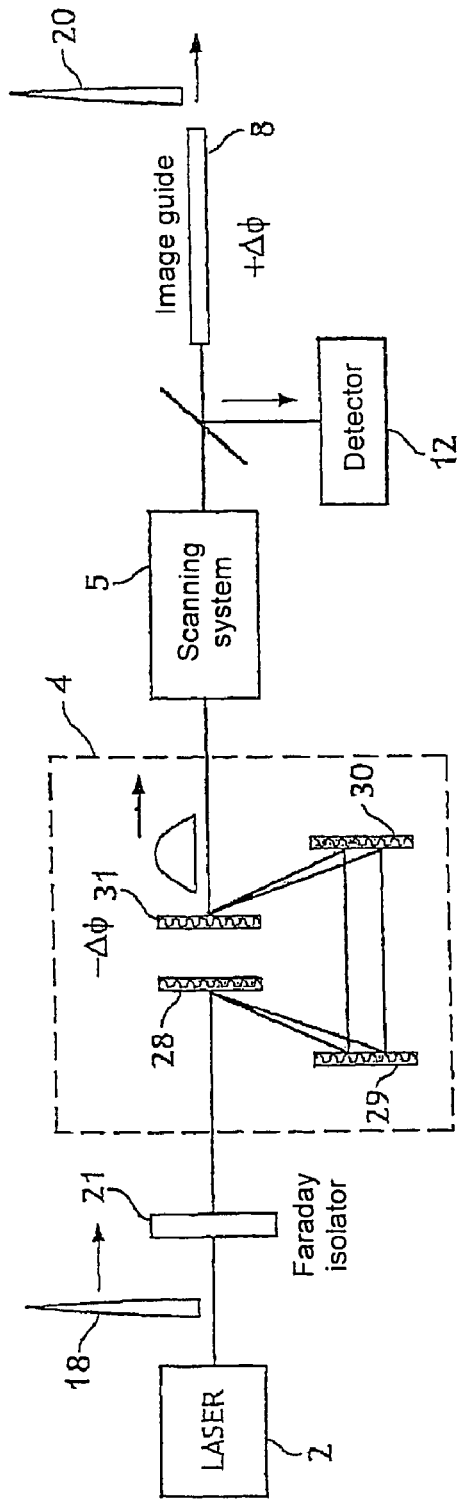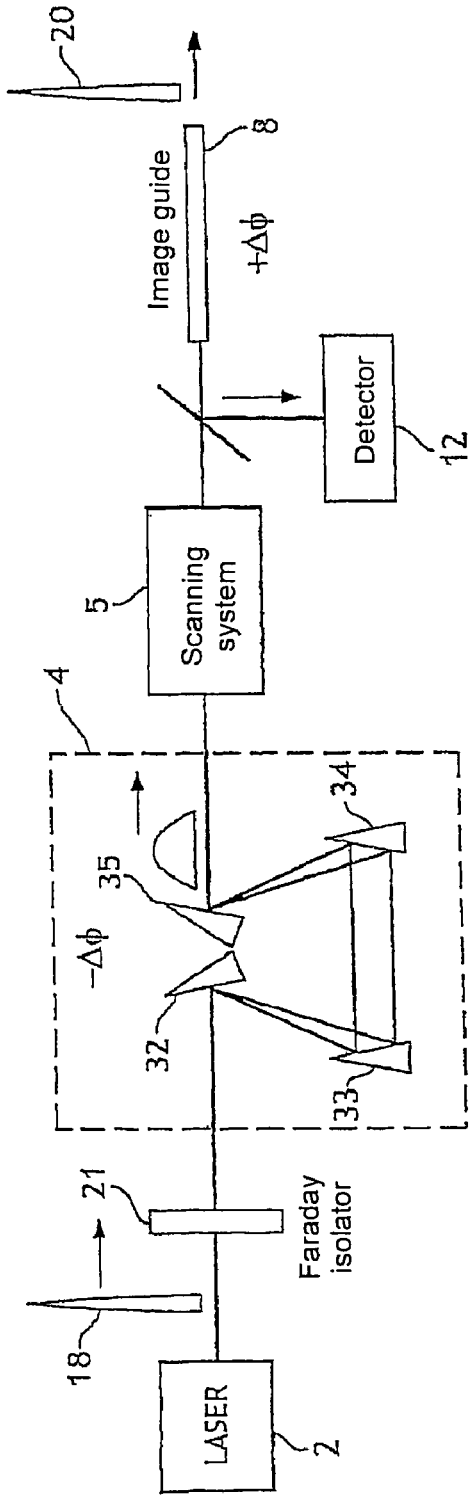

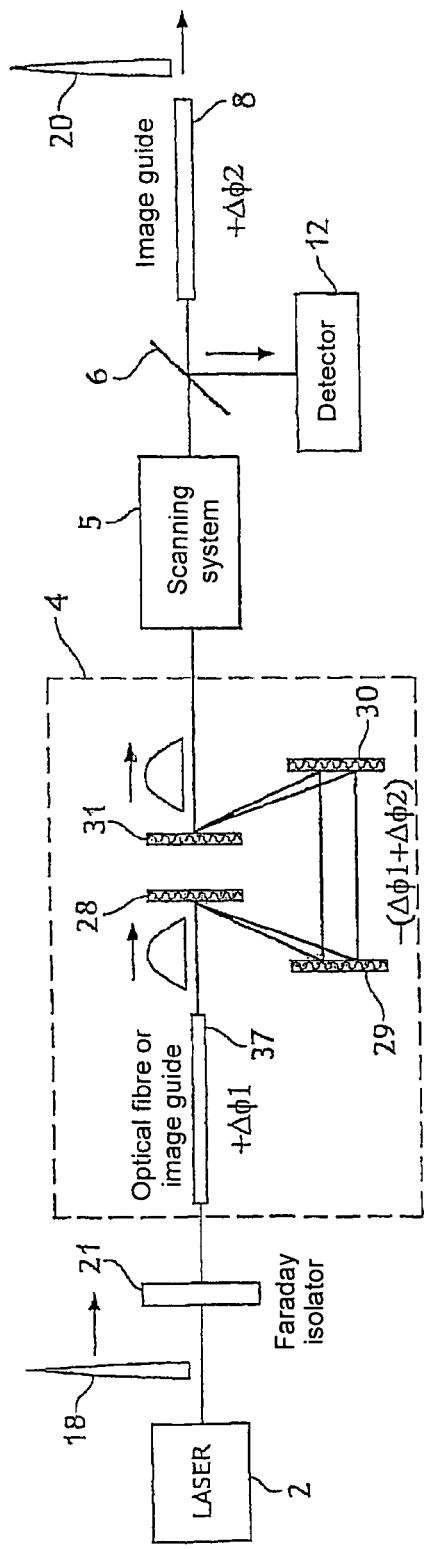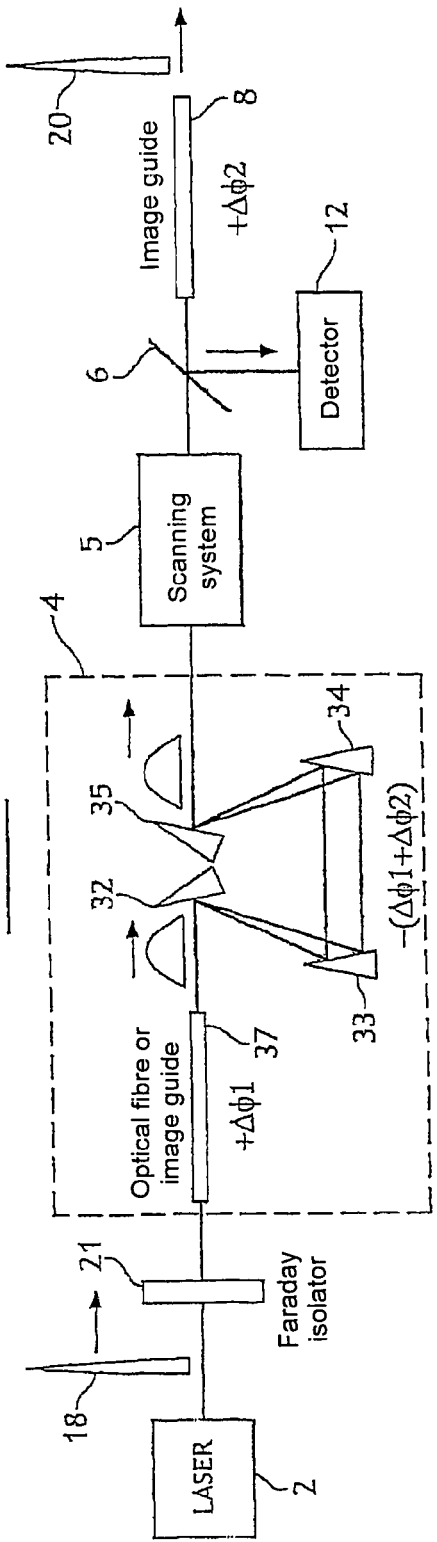

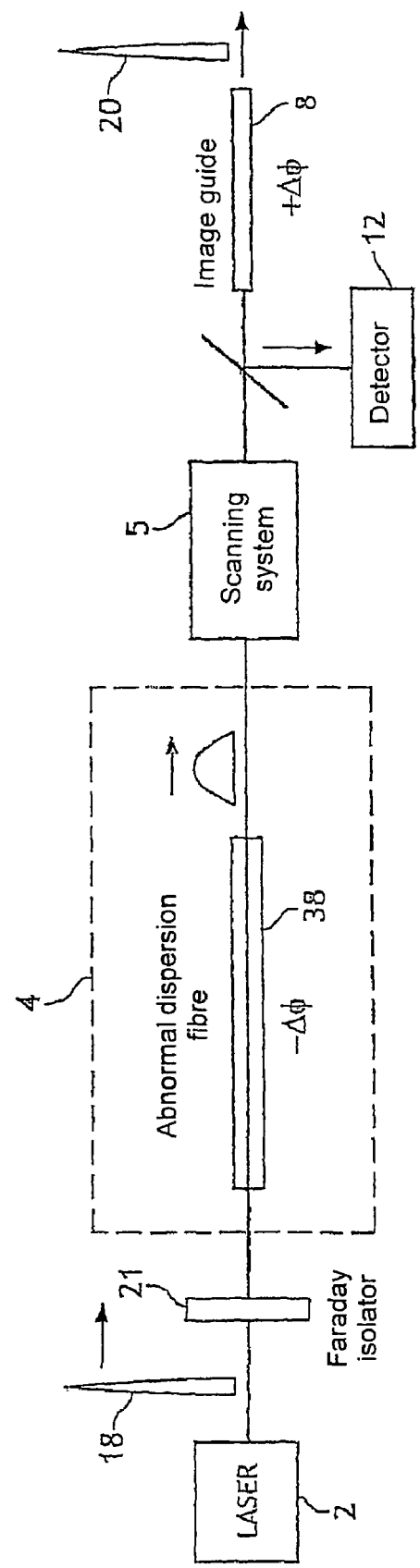

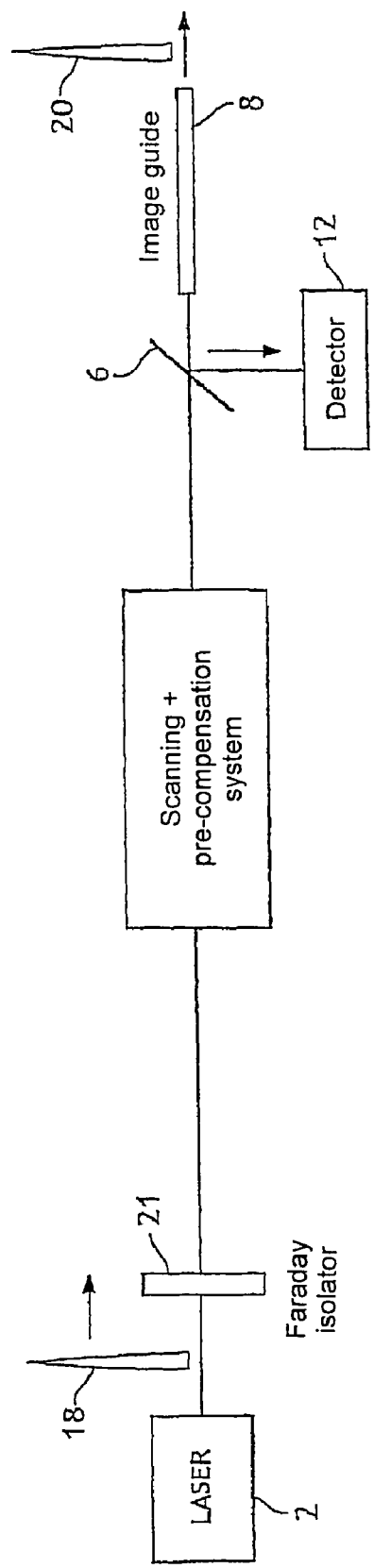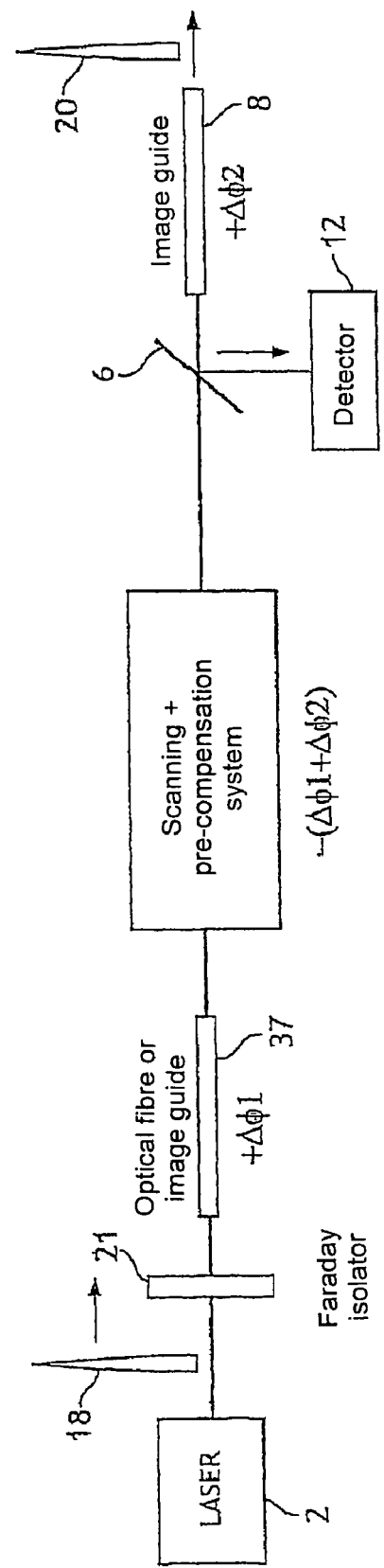

SYSTEM AND METHOD FOR CARRYING OUT FIBRE-TYPE MULTIPHOTON MICROSCOPIC IMAGING OF A SAMPLE

This invention relates to a system and a method for producing a fibre-type multiphoton microscopic image of a sample, for use in endoscopy or fluorescence microscopy. The field of application targeted is more specifically that of in vivo and in situ imaging.

In conventional confocal fluorescence imaging, a photon excites a molecule. The deexcitation of the latter causes the radiation of a fluorescent photon. The energy of the excitation photon corresponds exactly to the quantity of energy necessary for raising the molecule to a given excited state. The source used is a laser emitting excitation photons in the visible range (between approximately 400 nm and 650 nm). In multiphoton microscopy, in other words non-linear fluorescence microscopy, and more particularly in two-photon microscopy, the quantity of energy required for the transition is provided, not by an excitation photon, but by two photons (or more in multiphoton imaging), each having an energy two times (or more) less than that of the conventional excitation photon. In fact, excitation photons are used in the near infrared (700 nm to 1000 nm) which are less energetic than the excitation photons in the conventional case. However, the fluorescent photon emitted by the molecule is identical to that emitted in the conventional case.

In two-photon (or multiphoton) microscopy the mechanisms involving two (or more) photons have an efficiency which is proportional to the square (or more) of the instantaneous intensity of the excitation source. A high excitation efficiency can only be obtained by means of significant spatial and time constraints. The spatial constraint involves an accurate focussing of the excitation beam in the tissue, or a high spatial density of the photons in the illumination focal volume. Two-photon microscopy therefore has a major advantage which is its natural confocality since all the fluorescence detected originates only from the elementary volume excited at depth. The fluorescence emitted is not an integral of the volume comprised between the surface of the sample and the elementary volume excited; this in particular makes it possible to limit any problem of photobleaching of the fluorophores situated between the surface and the focussing plane. The time constraint involves a laser source generating ultra short and very intense pulses, i.e. a high time density of the photons in the illumination focal volume.

Moreover, as regards illumination standards, two-photon microscopy is appreciable since the near infrared produces less photons-matter interaction, and a pulsed excitation with ultra short pulses considerably reduces the problems associated with phototoxicity.

A drawback in fibre-type linear fluorescence microscopy resides in the fact that the penetration distance of the excitation beam into the sample is low, less than about a hundred micrometers. An increase in the power of these beams with a view to improving the penetration distance would certainly cause physiological damage, in particular due to the fact that generally the operation is carried out virtually continuous. Thus, organs lying at greater depth in the sample are not accessible. Two-photon microscopy makes it possible to overcome this drawback since it allows a theoretical penetration distance greater than 400 micrometers. In fact, the excitation photons, situated in the near infrared, are individually less energetic, poorly absorbed by the tissue which is essentially composed of water and therefore not very destructive compared with those used in linear fluorescence.

The two-photon microscopy systems commonly used are table microscopes such as for example an upright microscope constituted by a raised optical carriage holding scanning and detection devices for constituting images. Such an acquisition system cannot be applied in particular to in vivo and in situ endoscopy. In fact, a table microscope is often bulky, uses standard lenses for the illumination and collection of the signal, requires that the animal be held under the lens, and requires long integration times (which means great sensitivity).

Document GB2338568, Optiscan, "Two-photon endoscope or microscope method and apparatus" proposing a two-photon microscopy device, is known. This device uses a single optical fibre for conveying the pulses from the laser to the sample. In order to limit the phenomenon of linear and non linear dispersion of the pulses in the optical fibre, compensation means, in particular by prisms, are disclosed.

The document U.S. Pat. No. 6,369,928, Optical Biopsy Technologies, describes a two-photon fluorescence scanning microscope for the acquisition of a microscopic image. This microscope comprises at least two optical fibres: each used as a source and also as a receiver of the fluorescence beam obtained by illumination of the other optical fibre. In particular, two characteristics of this system constitute constraints for miniaturization: 1) the scanning takes place on the distal side of the fibres, i.e. between the fibres and the sample; 2) the two incident beams maintain an angle of incidence in the sample, therefore a distance between the fibres.

The purpose of the present invention is a novel miniaturized multiphoton microscopy system for an application in endoscopy in particular. Another purpose of the invention is a novel multiphoton microscopy system allowing the acquisition of an image in the sample at depth.

At least one of the above-mentioned aims is obtained with a system for fibre-type multiphoton imaging of a sample, in particular for use in endoscopy or in fluorescence microscopy, this system comprising a pulsed laser for generating a multiphoton excitation laser beam. According to the invention, this system also comprises:

an image guide constituted by a plurality of optical fibres and allowing the sample to be illuminated by a point-by-point scanning, in particular in a subsurface plane, compensation means for compensating for the dispersion effects of the excitation pulse in the image guide, these means being arranged between the pulsed laser and the image guide, scanning means for directing in succession the excitation laser beam into a fibre of the image guide.

Preferably, in order to obtain significant depths, the system comprises an optical head to focus the excitation laser beam leaving the image guide into the sample.

Preferably, the dimensions of the optical head and the image guide are such that they can easily slide into an operating channel.

The system according to the invention allows the production of an offset in vivo, in situ, fluorescence image with a microscopic resolution. The image guide or "fiber bundle", has a flexibility and a size which allow an application in endoscopy in particular by insertion into an operating channel.

According to an advantageous characteristic of the invention, different compensation means can be envisaged, such as for example:

a dispersive line containing at least two prisms;
a dispersive line containing at least two diffraction gratings;

a dispersive line containing means for modulating the phase and the spectral amplitude of the pulse;

another image guide, called a second image guide, which is associated with a dispersive line containing at least two prisms or two diffraction gratings, so that the phase shifts introduced by this second image guide and the principal image guide are compensated for by the phase shift introduced by the dispersive line;

a single optical fibre making it possible to optimize the response of the image guide, this single optical fibre being associated with a dispersive line containing at least two prisms or two diffraction gratings, so that the phase shifts introduced by this single optical fibre and the image guide are compensated for by the phase shift introduced by the dispersive line; or an optical fibre with abnormal dispersion at the laser wavelength.

These compensation devices can also serve to compensate for dispersions introduced by any other element (optical head, lenses, mirrors, etc.) of the system.

According to the invention, injection means are provided which are arranged on the proximal side of the image guide and making it possible to focus in succession the excitation laser beam into a given fibre of the image guide. First detection means for detecting a fluorescence signal originating from the sample are also provided. According to an advantageous characteristic of the invention, second detection means are also provided for detecting a second harmonic generation (SHG) signal originating from the sample. The complementarity between the properties of two-photon fluorescence and second harmonic generation makes it possible to access in particular local information about the molecular orders (symmetry, organization) and their interaction with their close environment.

In order for the signals originating from the sample to reach these detection means, the system also comprises a dichroic filter which is able to allow only the fluorescence and second harmonic signals to pass through to the detectors. In particular, this dichroic filter is arranged between the scanning means and the image guide. Thus, the signals originating from the sample do not pass through the scanning means again. In the same way, it is not necessary to arrange a filtering hole in front of each detector. In this case one takes advantage of the fact that multiphoton microscopy has a natural confocality.

The system according to the invention can also comprise a tunable dichroic filter which is able to separate the fluorescence signal from the second harmonic generation signal originating from the sample.

Generally, the system comprises a processing unit which manages all of the elements, in particular the synchronization between the excitation means and the detection means. This unit carries out an image processing which can for example be based on that described in the document WO 2004/008952, Mauna Kea Technologies. For example it is possible to control a slow scanning of the sample so as to produce high quality images integrating a large number of photons over a long time. However, according to an advantageous embodiment of the invention, the scanning means scan the sample at a speed corresponding to the acquisition of a number of images per second sufficient for a use in real time. In a complementary manner, the detection means detect the fluorescence signal at a detection frequency corresponding to a minimum sampling frequency of the fibres one-by-one. More precisely, respecting the sampling of the fibres (according to the Shannon criterion) makes it possible to obtain a point-by-point image which corresponds well to each fibre. This makes it possible to not lose information by sampling all of the fibres one-by-one while respecting a mean minimum number of images per second, namely in practice at least 12 images per second for a maximum mode of 896×640 pixels. The choice of the detection frequency (bandwidth of the detector) as a function of this minimum sampling then makes it possible for each fibre to detect the largest possible number of fluorescence photons. Thus, according to a possible embodiment, using an image guide with approximately 30,000 flexible optical fibres, the sampling frequency and the bandwidth of the detection system (an avalanche photodiode or equivalent) are set to approximately 1.5 MHz, corresponding approximately to 12 pixels per fibre, then making it possible to obtain at least the 12 images/s in maximum mode 896×640 pixels. In practice, the deflection of the beam is adjusted by determining a rapid scanning frequency of a "line" resonant mirror and a slow scanning frequency of a "frame" galvanometric mirror. This allows an appropriate rapid scanning of the fibres in order to obtain an image in real time.

The galvanometric mirrors can also have scanning frequencies suitable for a slow acquisition; in this case, the photodetector has a bandwidth suited to the slow acquisition speed.

According to the invention, the scanning means can also scan the sample on a line in a subsurface plane so as to produce a linescanning. It is thus possible to measure the intensities or speeds of certain elements observed.

The pulsed laser can be a femtosecond laser or a picosecond laser. The choice of a type of laser depends on the type (in terms of sensitivity in particular) of fluorescence targeted. For example, a picosecond laser has longer pulses and is therefore a laser which is a priori useful for high yield fluorophores. In fact, it is possible to use for example pulse widths comprised between 10 picoseconds and 10 femtoseconds.

Moreover, according to the invention, the pulsed laser and the compensation means are tunable as regards wavelength. Thus a laser can be used the wavelength of which can vary between 700 nm and 1000 nm, preferably between 800 nm and 870 nm, which already allows a large number of fluorophores to be detected. At each wavelength of the laser, the compensation is adjusted.

According to another feature of the invention, a method of fibre-type multiphoton imaging of a sample is proposed, in particular for use in endoscopy or in fluorescence microscopy, in which a multiphoton excitation laser beam is generated. According to the invention:

the excitation laser beam is passed through compensation means making it possible to compensate for dispersion effects, the sample is scanned by directing in succession the excitation laser beam into a fibre of an image guide constituted by a plurality of optical fibres, the sample is illuminated by a point-by-point scanning from the excitation laser beam originating from the image guide, and a fluorescence signal emitted by the sample is detected.

Advantageously, the entire fluorescence signal leaving the image guide is detected. Thus there is no de-scanning and the fluorescence signal is not filtered before detection by a photodetector.

In a variant of the invention without an optical head, the image guide is constituted by several thousands of optical fibres the distal ends of which are intended to be placed bare directly in contact with the surface of the sample, each fibre being able to produce a divergent beam capable of exciting a micro-volume from the sample situated from the surface to a maximum depth depending in particular on the core diameter of the optical fibres. Over the first ten micrometers for example, the beam also has a diameter which is more or less identical to the diameter of the core of the optical fibre. For an image guide called probe "S", the diameter of the optical fibres used is sufficiently small, for example 1 micrometer, for the multiphoton phenomenon to appear.

This variant therefore differs from the variant with an optical head in that it does not provide the scanning of a signal which is focussed at the output of each fibre but the scanning of a divergent signal at the output of each fibre. The non focussing of the signal at the fibre output makes it possible to obtain images of a volume situated just under the surface of the tissue which can be exploited and are interesting from a medical point of view in particular. These images are not "confocal" since they do not originate from a subsurface planigraphic plane scanned point-by-point, but are images that may however be qualified as "highly resolved" since they are produced by the scanning in succession micro-volumes situated directly under the surface.

One of the advantages of such a variant resides in the fact that for an endoscopic application, the diameter of the endoscopic probe can be very small depending solely on the diameter of the image guide and therefore on the number of its optical fibres. This makes it possible to envisage fields of application, such as for example the field of neurology, where the size of the endoscopic probe is a critical factor in overcoming inherent problems in the miniaturization of the focussing optical head.

According to another advantageous characteristic of the invention, the system comprises filtering and detection means for respectively separating and detecting several fluorescence signals emitted by several fluorophores which are present in the sample and which are excited by the excitation laser beam. In fact, ideally a pulsed laser beam is generated the wavelength of which has been determined in order to excite a given fluorophore. However, other fluorophores can be sensitive to this wavelength, and then also emit fluorescence signals. It is also possible to deliberately introduce fluorophores and to use a wavelength of the laser beam capable of exciting these fluorophores simultaneously. Preferably, the fluorescence signals have wavelengths which are sufficiently distanced from one another that they can be separated by filtering. The system comprises processing means for producing a final image comprising coloured zones as a function of the fluorescence signals of the fluorophores. The present invention is therefore able to carry out multimarking by detection path. The filtering means can comprise a tunable band-pass filter which allows the different fluorescence signals to pass sequentially towards a common detector. The filtering means can also comprise a separator which is able to send, as a function of the wavelength, each fluorescence signal towards a different detector.

According to yet another advantageous characteristic of the invention, the system also comprises a spectrometer which is able to produce a spectrum using a part of the signal originating from the sample. This spectrometer can be combined with a shutter directing a part of the signal originating from the sample towards the spectrometer at predetermined times corresponding to the times when the excitation signal scans an area of interest. Alternatively, it is also possible to control the pulsed laser in such a way that only the areas of interest are illuminated. The spectrum produced is then processed within the processing means. The part of the signal deflected towards the spectrometer is preferably less than 10% of the useful signal.

Other advantages and characteristics of the invention will become apparent on examining the detailed description of an embodiment which is in no way limitative, and the attached drawings, in which:

FIG. 4 is a diagrammatic top view of a system according to the invention provided with compensation based on four diffraction gratings;

FIG. 5 is a diagrammatic top view of a system according to the invention provided with compensation based on four prisms;

FIG. 10 illustrates a system equivalent to that described in FIG. 4 with, in addition, a dispersive section of optical fibre or image guide;

FIG. 11 illustrates a system equivalent to that described in FIG. 5 with, in addition, a dispersive section of optical fibre or image guide;

FIG. 12 is a diagrammatic top view of a system according to the invention provided with compensation based on optical fibre with anomalous dispersion;

FIG. 13 is a diagrammatic top view of a system according to the invention in which the scanning system and the compensation device are combined; and FIG. 14 illustrates an equivalent system to that described in FIG. 13 with, in addition, a dispersive section of optical fibre or image guide.

Figure 1:
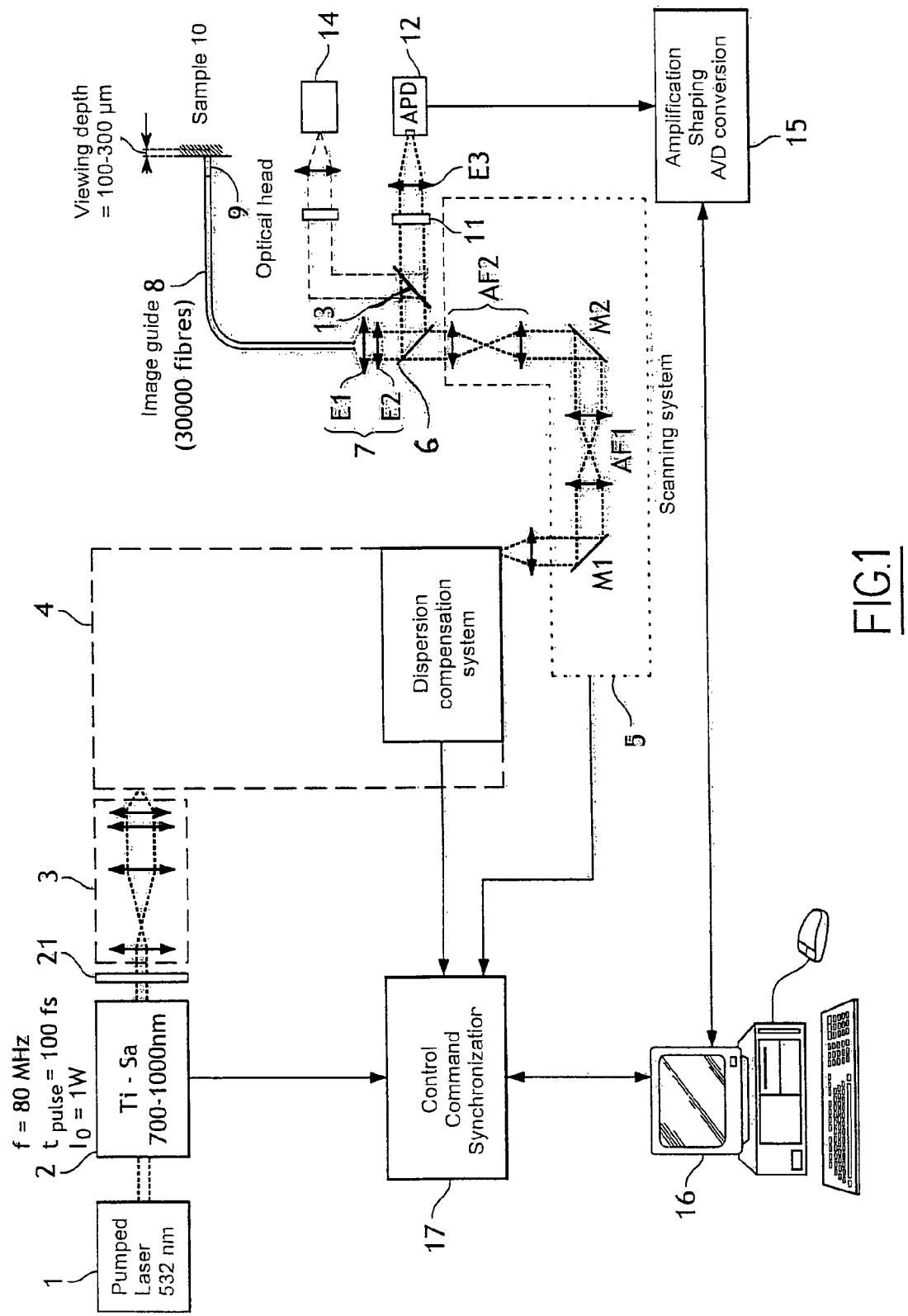
FIG. 1 is a diagrammatic view of the acquisition system according to the invention.

In FIG. 1 a sample 10 is seen which can be a biological tissue or a cell culture. Generally, the fluorescence observed can originate from an exogeneous compound (typically an administered marker) or an endogenous compound which is either produced by cells (transgenic type marker) of a biological tissue, or naturally present in the cells (autofluorescence).

Non-linear two-photon absorption requires a very high energy density to be conveyed into a reduced volume. For this purpose, a pulsed laser 2 is used in femtosecond regime with pulse widths of 100 fs. It is a Titanium-Sapphire laser pumped by a 1 to 532 nm solid laser. The repetition frequency of the laser 2 is approximately 80 MHz with an average power of the order of 1 Watt. The wavelength of the excitation beam leaving the laser 2 can be adjusted between 700 and 1000 nm, near infrared, preferably between 800 nm and 870 nm. In fact, the performance of the system depends essentially on the characteristics of the source: peak power and pulse width desired in particular at the output of the image guide.

At the output of the laser 2 a Faraday isolator 21 is provided in order to prevent the stray reflections from returning to the laser cavity 2. The isolator 21 is optionally followed, when necessary, by a device 3 for shaping and injection of the excitation laser beam. This device 3 is constituted by an afocal optical magnification system different from 1, comprising lenses which allow modification of the diameter of the laser beam. The magnification is calculated such that the diameter of the laser beam is suited to injection means provided for directing this laser beam into compensation means 4. These compensation means are adjusted as regards position and angle as a function of the wavelength of the excitation beam.

Generally, the function of the compensation means 4 is to pre-compensate the broadening of the excitation pulses in the optical fibres of the image guide 8. This temporal broadening is due to the linear chromatic dispersion and to the non-linear effects of the optical fibres (self-phase modulation causing a spectral broadening). The system makes it possible to obtain a pulse width at the output of the image guide 8 of a few hundreds of femtoseconds with an average power of a few tens of milliwatts.

Scanning means 5 then recover the thus pre-compensated excitation pulses. According to the example chosen and represented in FIG. 1, these means include a resonant mirror M1 at 4 KHz serving to deflect the beam horizontally and therefore to produce the lines of the image, a galvanometric mirror M2 at 15 Hz, generally between 10 and 40 Hz, serving to deflect the beam vertically and therefore to produce the frame of the image; and two afocal unit-magnification systems, AF1 situated between the two mirrors and AF2 situated after the mirror M2, these afocal systems being used in order to conjugate the planes of rotation of the two mirrors M1 and M2 with the plane of injection into one of the fibres. According to the invention, the scanning speed is determined in order to allow an observation of the tissues in vivo in situ. For this purpose the scanning must be sufficiently rapid so that there are at least 12 images/s displayed on the screen for a display mode of 896×640 pixels corresponding to the slowest mode. For display modes having less pixels, the number of images acquired per second is thus still greater than 12 images/s. In a variant, the scanning means can comprise in particular a rotary mirror, integrated components of the MEM type (X and Y scanning mirrors), or an acousto-optic system.

The mirrors M1 and M2 can also be two galvanometric mirrors the scanning frequencies of which are such that less than ten images per second are used, for example 1 to 3 images per second. In this case, the bandwidth of the associated photodetector is adjusted to the speed of acquisition imposed by the galvanometric mirrors. The integration time can be long so as to increase the sensitivity of the system.

The excitation beam deflected at the output of the scanning means 5 is directed towards the optical means 7 in order to be injected into one of the fibres of the image guide 8. The dichroic filter 6 arranged between the scanning means 5 and the injection means 7 remains transparent to the excitation beam. The injection means 7 are constituted here by two optical units E1 and E2. The first optical unit E1 allows partial correction of the optical aberrations at the edge of the field of the scanning means 5, the injection being thus optimized over the entire optical field, at the centre and at the edge. The second optical unit E2 is intended to carry out the injection itself. Its focal length and its numerical aperture have been chosen in order to optimize the rate of injection into the optical fibres of the guide 8. According to an embodiment which makes it possible to obtain the criterion of achromaticity, the first unit E1 is constituted by a doublet of lenses, and the second unit E2 by two doublets of lenses followed by a lens situated close to the image guide. In a variant, these injection optics could be constituted by any other type of standard optics, such as for example two triplets, or by lenses with a graded index (with a correction of the chromatism by diffractive optical elements) or by a microscope lens.

The image guide 8 is constituted by a very large number of flexible optical fibres, for example 30,000 fibres made of germanium-doped silica, each single-mode, of 2 μm diameter, with a numerical aperture of 0.23 and spaced at intervals of 3.8 μm relative to its neighbour. The cross section of the guide is of the order of 0.8 mm. In practice, it is possible to use either all of the fibres of the image guide, or a sub-unit chosen from these fibres, for example centred. In a variant, the image guide can comprise multimode fibres of 1.9 μm diameter, with a numerical aperture of 0.42 and spaced at 3.3 μm for a cross section of the guide of the order of 0.65 mm.

The distal end of the optical fibre is connected to an optical head 9 which focuses the excitation laser beam into the sample 10 in an elementary volume. This elementary volume or point is situated at a given depth located at a few hundreds of μm from the surface of the sample which the optical head 9 is intended to be placed in contact with. This depth can be for example 200 μm. The optical head 9 therefore makes it possible to focus the flux leaving the image guide into the sample, but also to collect the flux of fluorescence returning from the sample. The optical head 9 has a magnification of 2.4 and a numerical aperture on the sample of 0.5. Since two-photon microscopy naturally has a confocal character, it is not necessary to filter the fluorescence signal collected by the photodetector: all the different fluxes of this signal are sent towards the photodetector, which improves the sensitivity of the system. With these magnification and numerical aperture values, the axial resolution is of the order of 15 μm and the lateral resolution of the order of 2 μm. The numerical aperture is also chosen in such a way as to optimize the number of photons recovered which must be as large as possible. The optical head can be constituted by standard optics (doublet, triplet, aspheric) and/or by lenses with a graded index (GRIN). During operation, the optical head is in particular intended to be placed in contact with the sample 10. In an optimal manner, the optical head comprises refractive optics with a magnification of 4 and a numerical aperture of 1. This optical head is of the water-immersion and non-achromatic type.

The fluorescence signal therefore passes through the image guide 8 and the injection means 7 then reflects off the dichroic filter 6 which directs this fluorescence signal towards a fluorescence detector 12 via a coloured rejection filter 11 and a focussing lens E3.

The dichroic filter 6 has a transmission efficiency of 98 to 99% at the excitation wavelength and therefore reflects the other wavelengths. The fluorescence signal, originating from the sample via the optical head and the image guide, is thus sent towards the detection path. The rejection filter 11 makes it possible to totally eliminate the 1 to 2% of stray reflections at the excitation wavelength and which still pass towards the detection path.

The detector 12 has a maximum sensitivity at the fluorescence wavelength studied. It is possible for example to use an avalanche photodiode (APD) or a photo multiplier. Moreover, according to the invention, the bandwidth is chosen in order to optimize the integration time of the fluorescence signal. It is 1.5 MHz in real time, which corresponds to the minimum sampling frequency of the image guide with an optimized integration time on each pixel.

The system according to the present invention is in particular remarkable by the fact that it makes it possible to combine second harmonic generation microscopy with multiphoton microscopy. It involves detecting the second harmonic generation signal emitted at the same time as the fluorescence signal by the sample. For this purpose, a tunable dichroic filter 13 or any other device is provided placed between the dichroic filter 6 and the rejection filter 11, and making it possible to separate the second harmonic generation signal from the fluorescence signal. A detector SHG 14 receives this second harmonic generation signal.

The electronic and computational means 16 (such as a micro-computer) for control, analysis and digital processing of the detected signal and for viewing include the following boards:

- a synchronization board 17, the functions of which are;
- to control in a synchronized manner the scanning, i.e. the movement of the line M1 and frame M2 mirrors;
- to control in a synchronized manner with the fluorescence images, the analysis of the data originating from the SHG detector 14;
- to know at all times the position of the laser spot thus scanned;
- to manage all the other boards by means of a microcontroller itself being able to be controlled; and
- to control the pre-compensation means so as to manage the wavelength tunability of the system;
- a detector board 15 which comprises for each detection path an analogue circuit which in particular produces an impedance match, an amplifier, an analogue-to-digital converter then a programmable logic component (for example an FPGA circuit) which shapes the signal.

The micro-computer 16 also comprises a digital acquisition board (not represented) which makes it possible to process a digital data flow at variable frequency and to display it on a screen using a graphics board (not represented).

By way of a non-limitative example the image processing used in the present invention can be a simple adaptation of the image processing as described in particular in the document WO 2004/008952 and/or the document WO 2004/010377.

As regards the case of an image guide without an optical head, the operation of the apparatus is the same as that described previously with the exception of the following: at the output of the guide, the divergent light emerging from the injected fibre is diffused in the sample and the fluorescence signal is collected in a micro-volume situated between the surface and a depth of a few μm (according to the core diameter of the fibres and their NA). Thanks to the scanning, the sample is illuminated micro-volume by micro-volume. At each moment, the micro-volume excited in the tissue then emits a fluorescence signal which has the characteristic of being shifted towards smaller wavelengths. This fluorescence signal is captured by the image guide, then follows the reverse path of the excitation beam as far as the dichroic filter 6 which will transmit the fluorescence signal towards the detection path. The signals detected, one after the other, are in particular processed in real time thanks to the same image processing as that described above with reference to FIG. 1 in order to allow the reconstruction of an image in real time viewed on the screen.

FIGS. 2 to 14 illustrate a few examples of pre-compensation devices. The pre-compensation consists in preparing the ultra-short laser pulse by providing it with the spectral width and the phase modulation which will lead to its optimum temporal compression at the output of the image guide 8. The technique used aims to compensate for the group velocity dispersion of the whole of the system and to also compensate for the inevitable non-linear effects which the light pulse undergoes during its propagation in the image guide 8. The pre-compensation principle envisaged conforms with that published by S. W. Clark, F. O. Ildlay, and F. W. Wise, "Fiber delivery of femtosecond pulses from a Ti:sapphire laser", Optics Letters Vol. 26, NO. 17, Sep. 1, 2001.

Typically the pre-compensation comprises two parts: a section of optical fibre followed by a dispersive line with diffraction gratings.

- the section of optical fibre constituted by a single optical fibre or an image guide: the single optical fibre used is single-mode for the laser wavelength. The length of the section is close to that of the multi-core image guide 8. This length is optimized as a function of the other parameters of the system such as for example the length of the image guide, the wavelength of the laser beam, the power and the width of the pulses at the input and at the output of the image guide, etc. The mode diameter of this fibre is greater than the mode diameter of the cores of the image guide in order to balance the non-linear effects encountered in the two parts of the pre-compensation. Thus an optical fibre with a large mode area (LMA) or belonging to the new generation of optical fibres with a structured air-silica cladding is used. This section of single-mode fibre is characterized by a certain rate of normal group velocity dispersion (principally of the order 2 and 3) and by the appearance of non-linear effects of spectral broadening (especially over the first millimeters of the section) which are controlled by the mode diameter. This section, constituted by a single optical fibre or a second image guide, provides the excitation laser pulses with a phase shift. This phase shift serves to pre-compensate the dispersion in the principal image guide 8, but it can also serve to compensate any other dispersion introduced by the rest of the system such as the optical head for example.

- the dispersive line with diffraction gratings: this part comprises two diffraction gratings, operating in reflection which are planar and have great efficiency, associated with a reflecting plane mirror which is totally reflective. The diffraction gratings face each other and are arranged parallel a few centimeters from one another. The laser beam successively strikes these two gratings with oblique incidence before reaching the plane mirror which reflects the light back approximately onto itself. The laser beam thus strikes the gratings four times before reemerging from the dispersive line. The aim of this dispersive line is to introduce a high rate of abnormal group velocity dispersion into the system. This equates to delaying the most red photons of the laser spectrum which corresponds to the reverse behaviour to that which occurs both in the section of single-mode fibre mentioned above but also in the image guide. This device known by the name "Treacy line" is widely used in amplification systems with frequency drift of femtosecond laser chains where it then plays the role of pulse compressor at the end of the chain. The dispersive line is characterized by a certain rate of abnormal group velocity dispersion (principally of the order 2 and 3) depending on the pitch of the gratings, the inter-grating distance and the angle of incidence on these gratings.

Figure 2:
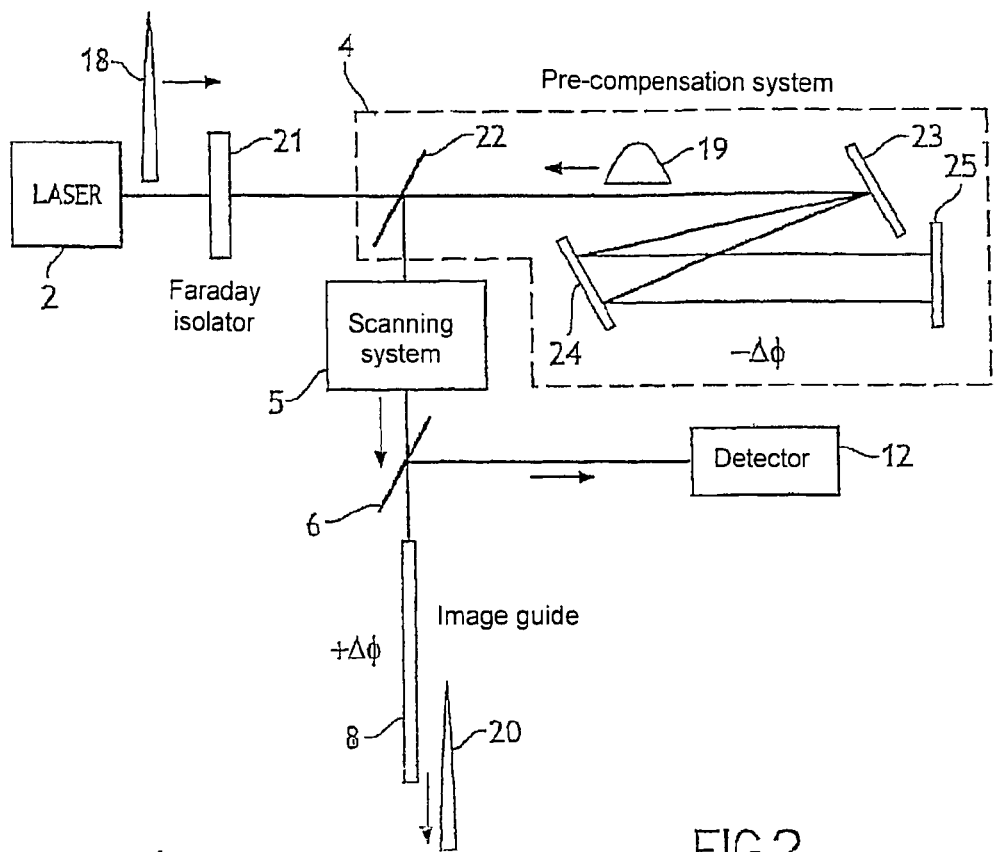
FIG. 2 is a diagrammatic top view of a system according to the invention provided with compensation based on diffraction gratings.

FIGS. 2 to 14 are simplified diagrams of the system according to the invention in which the pre-compensation device 4 is shown in detail. For the sake of clarity, the device 3 does not appear. The same elements of FIG. 1 are shown again in FIGS. 2 to 14 with the same references. The laser 2, the scanning system 5, the dichroic filter 6 which transmits the excitation beam towards the sample and which returns the fluorescence signal to the detector 12 are seen. FIGS. 2 to 7 illustrate basic compensation devices not comprising a first section. The beam leaving the Faraday isolator 21 is directed directly towards a dispersive line with diffraction gratings or prisms. In FIG. 2, this line comprises two diffraction gratings 23, 24 and a mirror 25. The course of the laser beam in the dispersive line is as follows: reflection off the first diffraction grating 23 towards the second diffraction grating 24, reflection off the second diffraction grating 24 towards the mirror 25 where it is totally reflected towards the second grating 24 then the first grating 23. The pulse 19 leaving the dispersive line is longer than that 18 leaving the laser 2. The beam originating from the diffraction grating 23 then reflects off the mirror 22 in the direction of the scanning system 5 then towards the image guide 8. FIGS. 2 to 14 are top views; in particular in FIGS. 2, 3, 6-9, the laser beam leaving the laser 2 towards the grating 23 passes above the mirror 22 without passing through it. By contrast, the laser beam from the grating 23 towards the scanning system is reflected off the mirror 22. This mirror 22 can be replaced by a separator which allows the excitation beam of the laser to pass towards the dispersive line and reflects the excitation beam of the dispersive line towards the scanning system, the two beams then being aligned. But, in this last case, the losses caused by the separators are significant (only 25% of the incident signal is used).

Figure 3:
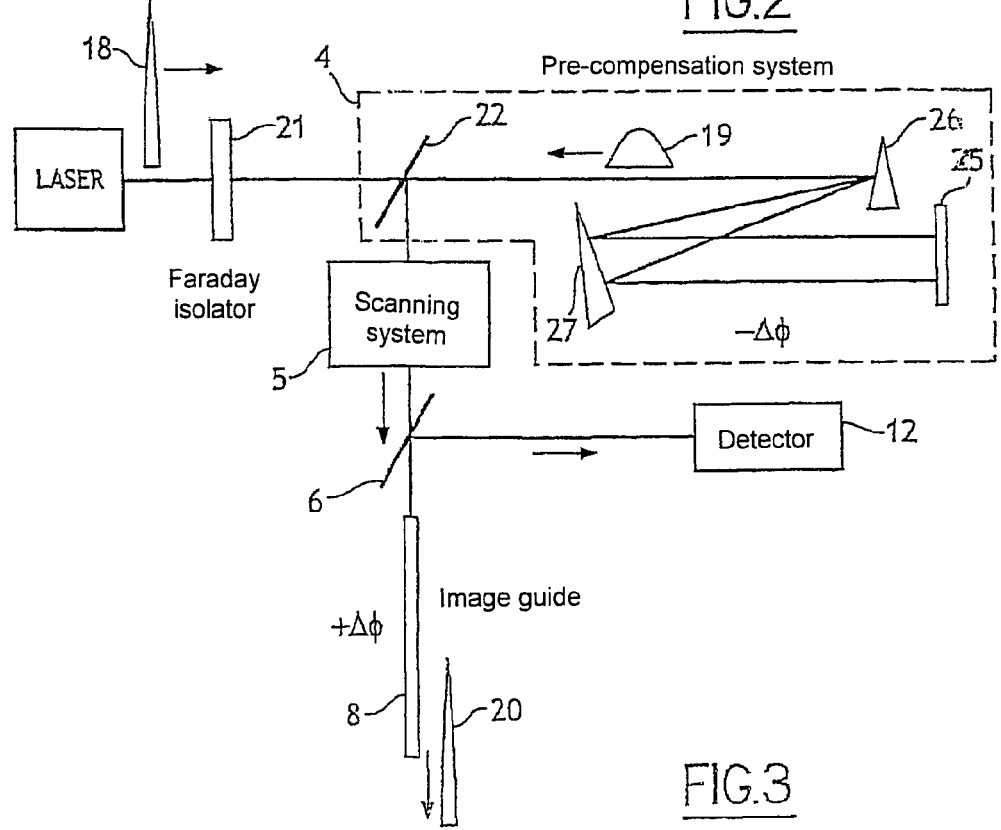
FIG. 3 is a diagrammatic top view of a system according to the invention provided with compensation based on prisms.

The linear dispersion and the non-linear effects in the image guide 8 modify the temporal and spectral profile of the excitation pulse which returns to being approximately identical to the profile 18 of the pulse leaving the laser 2. The dispersive line provides a phase shift of $-\Delta\phi$ so as to approximately compensate for the phase shift $+\Delta\phi$ provided by the image guide 8. In FIG. 3, the two diffraction gratings are replaced by two prisms 26 and 27, the course of the excitation laser beam is identical.

In FIGS. 4 and 5, the dispersive line and the mirror 22 are replaced by respectively four diffraction gratings for FIG. 4 and four prisms for FIG. 5. The excitation laser beam is reflected successively off the four diffraction gratings 28, 29, 30 and 31 (prisms 32, 33, 34 and 35).

Figure 6:
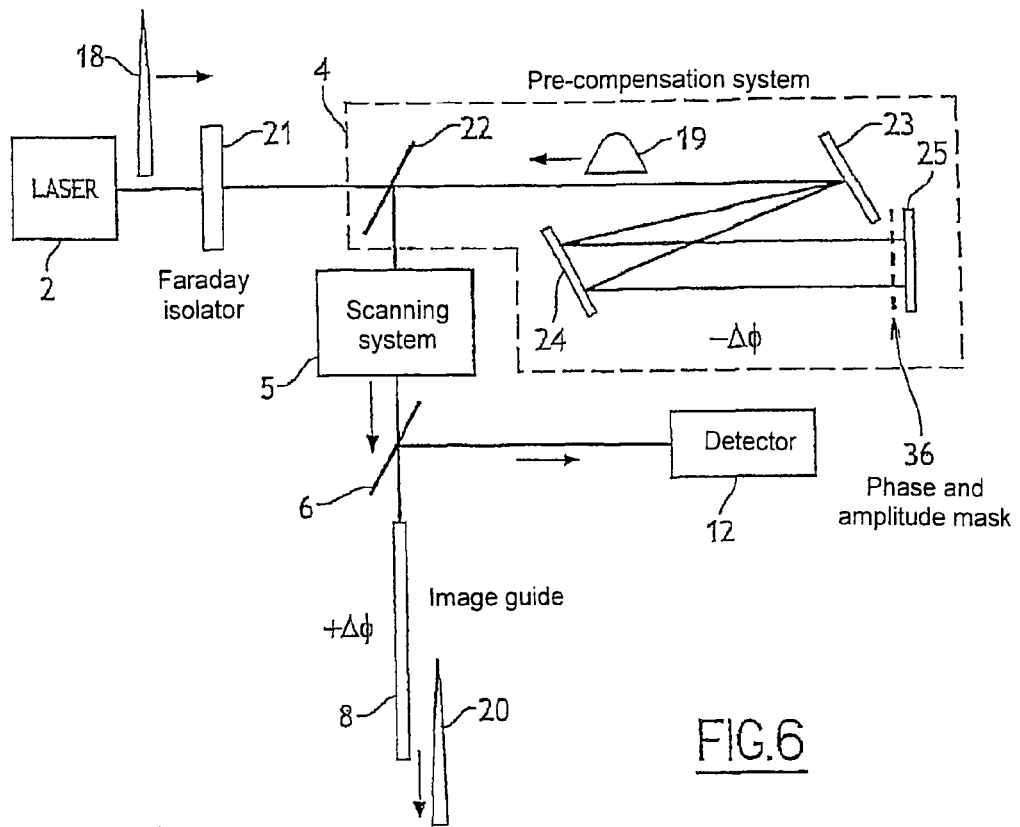
FIG. 6 illustrates a system equivalent to that described in FIG. 2 with, in addition, a phase mask and an amplitude mask which effects the shape of the pulse as regards phase and amplitude.
Figure 7:
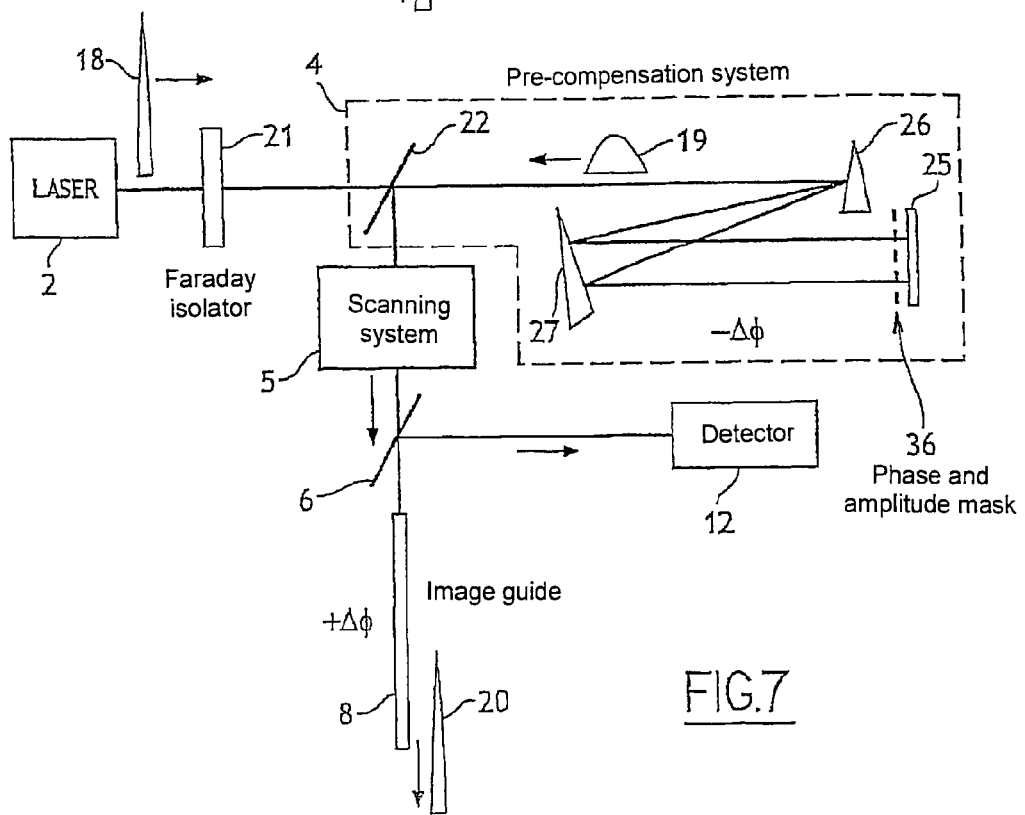
FIG. 7 illustrates a system equivalent to that described in FIG. 3 with, in addition, a phase mask and an amplitude mask which effects the shape of the pulse as regards phase and amplitude.
Figure 8:
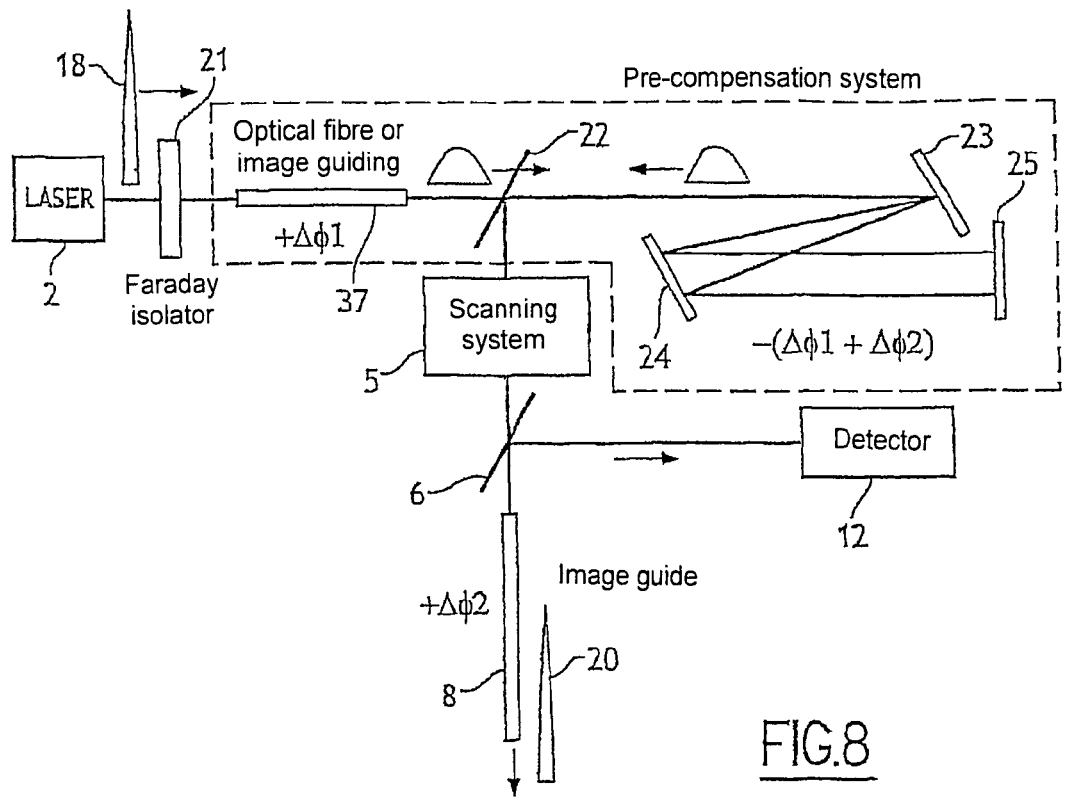
FIG. 8 illustrates a system equivalent to that described in FIG. 2 with, in addition, a dispersive section of optical fibre or image guide.
Figure 9:
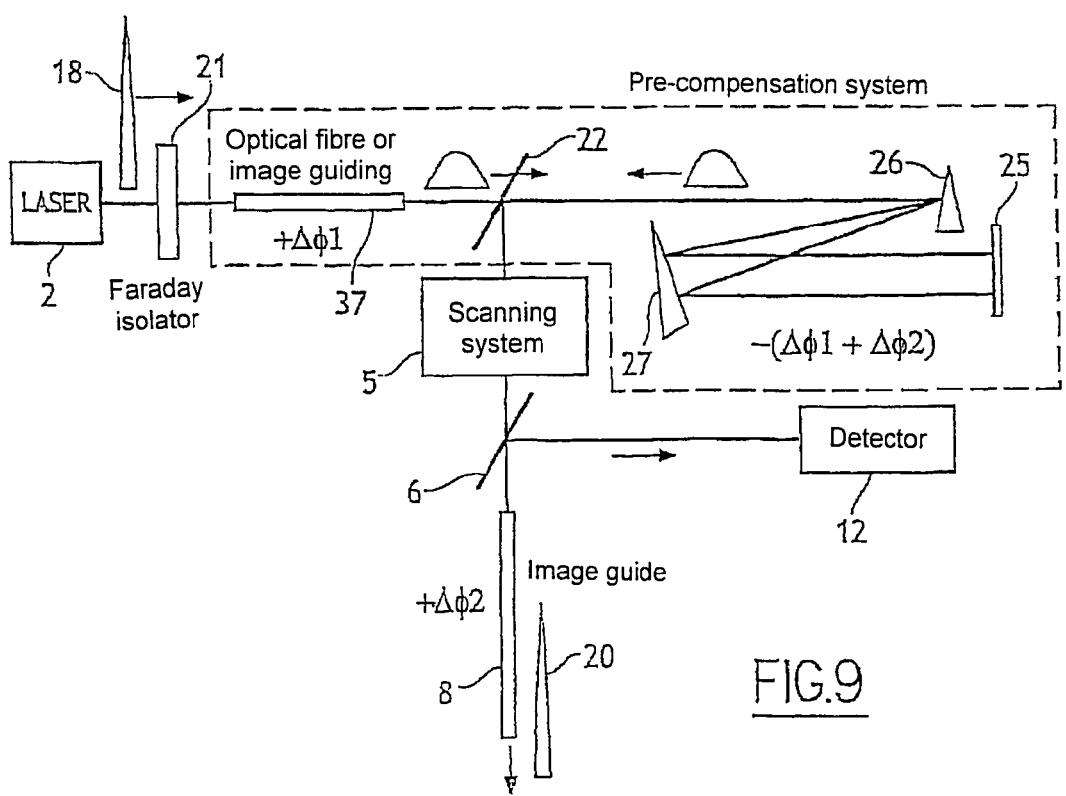
FIG. 9 illustrates a system equivalent to that described in FIG. 3 with, in addition, a dispersive section of optical fibre or image guide.

FIGS. 6 and 7 correspond to FIGS. 2 and 3 in which a phase and amplitude mask 36 has been introduced upstream of the mirror 25. This mask makes it possible to improve the pre-compensation performance by precisely adjusting the shape of the pulse relative to the dispersion of the image guide. It can be constituted by the assembly of different glass slides acting on the spectral phase and by a filter which can be varied in a transverse manner and acting on the spectral amplitude.

FIGS. 8 to 11 correspond respectively to FIGS. 2 to 5 but with in addition a section 37 arranged either upstream of the mirror 22 (FIGS. 2 and 3) or upstream of the four diffraction gratings (FIG. 4) or of the four prisms (FIG. 5).

This section can be constituted by a single optical fibre or an image guide wherein the characteristics of each optical fibre constituting it are approximately identical to those of the principal image guide.

This single optical fibre or second image guide provides a positive phase shift $+\Delta\phi 1$. The image guide 8 also provides a positive phase shift $+\Delta\phi 2$. Thus, the dispersive line (FIGS. 8 to 11) provides a negative phase shift of $\Delta\phi 1+\Delta\phi 2$).

As seen in FIG. 12, the pre-compensation stage can also be obtained using a single section 38 of optical fibre with abnormal dispersion at the laser wavelength. This specific fibre has a nil dispersion at shorter wavelengths than that of the laser wavelength. This is obtained by using a section of new-generation fibre with an optimized length having one of the following structures:—concentric dual-core fibres, fibre with a structured air-silica cladding, photon fibre with a hollow core and with a structured air-silica cladding, photon fibre with a hollow core and with a Bragg cladding. This section of pre-compensating fibre is also characterized by a mode diameter which is optimized in order to take into account the non-linear effects associated with the propagation in this waveguide.

In a variant of the above, the pre-compensation can be integrated into the scanning system as can be seen in FIGS. 13 and 14. In fact, any one of the compensation devices described in FIGS. 2 to 11 can be inserted on an optical path in the scanning system 5.

This invention therefore relates to a microscope based on an image guide the advantages of which are the compactness and the flexibility, which allows a use in endoscopy by insertion of said image guide into the tissue. Finally, the combination of multiphoton microscopy with a fibre-type microscopy by means of an image guide allows the acquisition of a fluorescence image of an element situated at depth in the sample observed. In practice, the system can be adaptable, i.e. designed without the laser source and thus being able to interface with laser sources already existing in laboratories.

This invention can have numerous applications, in particular where non-invasive or slightly invasive methods are required. These applications are for example urethral endoscopy when an optical probe with a diameter less than 1 mm is inserted into a bladder for example; colonoscopy in small animals; viewing of the cornea and the retina; viewing of the muscle fibres and the nerves; microcirculation of leukocytes and blood flow; vascular and renal architecture; the membranes of hepatic cells; and in situ neurobiology for viewing the deep cerebral structures of live small animals for example or potential clinical applications for humans.

Of course, the invention is not limited to the examples which have just been described and numerous adjustments can be made to these examples without exceeding the scope of the invention.

The invention claimed is:

1. A system for carrying out fibre-type multiphoton imaging of a sample, comprising:
    a pulsed laser for generating a multiphoton excitation laser beam;
    an image guide comprising a plurality of optical fibres to allow the sample to be illuminated by a point-by-point scanning,
    a compensation device configured to compensate for non-linear effects and dispersion effects of excitation pulses in the image guide, the compensation device comprising:
        a section of optical fibre followed by a dispersive line,
            wherein the section of optical fibre comprises an optimized length and a mode diameter greater than the image guide fibre mode diameters, and
            wherein the optimized length is a function of at least a wavelength of the laser beam, a power and a width of pulses at an input and an output of the image guide, and a length of the image guide;
        wherein the compensation device is arranged between the pulsed laser and the image guide; and
    a scanning device positioned in the system after the section of optical fibre of the compensation device and before the image guide, for directing in succession the multiphoton excitation laser beam into individual fibres of the image guide.

2. The system according to claim 1, wherein the compensation device comprises the dispersive line containing at least two prisms.

3. The system according to claim 2, wherein the dispersive line ends with a mirror upstream of which a phase and amplitude mask is arranged.

4. The system according to claim 1, wherein the compensation device comprises the dispersive line containing at least two diffraction gratings.

5. The system according to claim 1, wherein the section of optical fiber comprises a second image guide, which is associated with the dispersive line containing at least two prisms, such that phase shifts introduced by the second image guide and the image guide are compensated for by a phase shift introduced by the dispersive line.

6. The system according to claim 1, wherein the section of optical fiber comprises a second image guide, which is associated with the dispersive line containing at least two diffraction gratings, such that phase shifts introduced by the second image guide and the image guide are compensated for by a phase shift introduced by the dispersive line.

7. The system according to claim 1, wherein the section of optical fiber comprises a single optical fibre associated with the dispersive line containing at least two prisms, such that phase shifts introduced by the single optical fibre and the image guide are compensated for by a phase shift introduced by the dispersive line.

8. The system according to claim 1, wherein the section of optical fiber comprises a single optical fibre associated with the dispersive line containing at least two diffraction gratings, such that phase shifts introduced by the single optical fibre and the image guide are compensated for by a phase shift introduced by the dispersive line.

9. The system according to claim 1, wherein the compensation device is integrated into the scanning device.

10. The system according to claim 1, wherein the pulsed laser and the compensation device are tunable as regards wavelength.

11. The system according to claim 1, further comprising an injection device arranged on a proximal side of the image guide to focus in succession the multiphoton excitation laser beam into the individual fibres of the image guide.

12. The system according to claim 1, further comprising a first detection device for detecting a fluorescence signal originating from the sample.

13. The system according to claim 1, further comprising a dichroic filter to direct the signals originating from the sample towards a detector.

14. The system according to claim 13, wherein said dichroic filter is arranged between the scanning device and the image guide.

15. The system according to claim 1, wherein the pulsed laser is a femtosecond laser.

16. The system according to claim 1, wherein the pulsed laser is a picosecond laser.

17. The system according to claim 1, wherein the image guide comprises a plurality of sequenced single-mode optical fibres.

18. The system according to claim 1, wherein the image guide comprises a plurality of multimode optical fibres.

19. The system according to claim 1, further comprising an optical head to focus the multiphoton excitation laser beam leaving the image guide into the sample.

20. The system according to claim 1, wherein the image guide comprises several thousands optical fibres, the distal ends of which are configured to be placed directly in contact with a surface of the sample.

21. The system according to claim 1, wherein the diameter of each of the plurality of optical fibres is about 2 micron.

22. A method for carrying out fibre-type multiphoton imaging of a sample, comprising:
generating, by a pulsed laser, a multiphoton excitation laser beam;
passing the multiphoton excitation laser beam through a compensation device to compensate for non-linear effects and dispersion effects, wherein the compensation device is arranged between the pulsed laser and an image guide comprising a plurality of optical fibres, wherein the compensation device comprises:
a section of optical fibre followed by a dispersive line, wherein the section of optical fibre comprises an optimized length and a mode diameter greater than the image guide fibre mode diameters,
wherein the optimized length is a function of at least a wavelength of the laser beam, a power and a width of pulses at an input and an output of the image guide, and a length of the image guide;
scanning, using a scanning device, the sample by directing in succession the multiphoton excitation laser beam into individual fibres of the image guide comprising a plurality of optical fibres, wherein the sample is illuminated by a point-by-point scanning from the multiphoton excitation laser beam originating from the image guide, and wherein the scanning device is positioned after the section of optical fibre of the compensation device and before the image guide; and
detecting a fluorescence signal emitted by the sample.

23. The method according to claim 22, wherein the entire fluorescence signal leaving the image guide is detected.

24. The method according to claim 22, wherein the diameter of each of the plurality of optical fibres is about 2 micron.

* * * * *